United States Patent
Stotler et al.

(10) Patent No.: US 8,859,011 B2
(45) Date of Patent: Oct. 14, 2014

(54) CALCIUM COMPOSITIONS

(75) Inventors: Denis Stotler, Cuba, MO (US); Steven R. Freebersyser, Florissant, MO (US); R. Saul Levinson, Chesterfield, MO (US)

(73) Assignee: Particle Dynamics International, LLC, St. Louis, MO (US)

(*) Notice: Subject to any disclaimer, the term of this patent is extended or adjusted under 35 U.S.C. 154(b) by 2053 days.

(21) Appl. No.: 11/746,832

(22) Filed: May 10, 2007

(65) Prior Publication Data

US 2007/0264329 A1    Nov. 15, 2007

Related U.S. Application Data

(60) Provisional application No. 60/800,178, filed on May 12, 2006.

(51) Int. Cl.

| | |
|---|---|
| *A61K 9/20* | (2006.01) |
| *A61K 33/10* | (2006.01) |
| *A61K 31/593* | (2006.01) |
| *A61K 9/16* | (2006.01) |
| *A23L 1/304* | (2006.01) |
| *A23L 1/03* | (2006.01) |
| *A23L 1/00* | (2006.01) |

(52) U.S. Cl.
CPC .............. *A61K 9/2059* (2013.01); *A61K 9/16* (2013.01); *A23L 1/304* (2013.01); *A23V 2002/00* (2013.01); *A61K 9/2027* (2013.01); *A61K 33/10* (2013.01); *A23L 1/0305* (2013.01); *A23L 1/0023* (2013.01); *Y10S 514/96* (2013.01)
USPC ............ 424/687; 424/464; 514/167; 514/960

(58) Field of Classification Search
None
See application file for complete search history.

(56) References Cited

U.S. PATENT DOCUMENTS

| | | | |
|---|---|---|---|
| 4,994,449 A | 2/1991 | Leonard | |
| 5,424,331 A | 6/1995 | Shlyankevich | |
| 6,818,228 B1 | 11/2004 | Walsdorf et al. | ............... 424/464 |
| 7,198,653 B2 | 4/2007 | Lang et al. | |
| 2004/0132771 A1 | 7/2004 | Babcock et al. | |
| 2005/0025811 A1 | 2/2005 | Levin et al. | .................... 424/429 |
| 2007/0003611 A1 | 1/2007 | Liu et al. | |

FOREIGN PATENT DOCUMENTS

| | | |
|---|---|---|
| WO | 2006092727 A2 | 9/2006 |
| WO | 2006092727 A3 | 9/2006 |
| WO | PCT/US2007/068650 | 5/2007 |

OTHER PUBLICATIONS

Behn, "Sodium Lauryl Sulfate" in Handbook of Pharmaceutical Excipients, 5th Edition, 2006, Pharmaceutical Press, pp. 687-689, article revised Aug. 15, 2006.*
Amethyst Galleries, "Limestone", downloaded from http://www.galleries.com/rocks/limestone.htm on Dec. 1, 2010, pp. 1-2 of 2.*
Haines-Nutt (1976) J. Pharm. Pharmac. 28: 468-470.
http://www.caltrate.com/products/caltrate600_lbl.asp: Caltrate Product Labeling, 2007, 2 pages.
PDR for Nutritional Supplements (2001), Thomson PDR; 74-79.

* cited by examiner

*Primary Examiner* — Savitha Rao
*Assistant Examiner* — Gregg Polansky
(74) *Attorney, Agent, or Firm* — Senniger Powers LLP

(57) ABSTRACT

Compositions comprising calcium carbonate and processes for making such compositions are provided. The invention provides a granulation comprising about 95% to about 99% by weight calcium carbonate, about 0.5% to about 5% by weight of a binder and about 0.03% to about 3% by weight of a porosity increasing agent. A pharmaceutical or nutritional composition prepared from such a granulation comprises about 90% to about 99% by weight calcium carbonate, about 0.03% to about 3% by weight of a porosity increasing agent, and about 1% to about 10% by weight of other excipients. The composition provides a smaller tablet than conventional calcium carbonate compositions, for improved ease of swallowing.

28 Claims, 1 Drawing Sheet

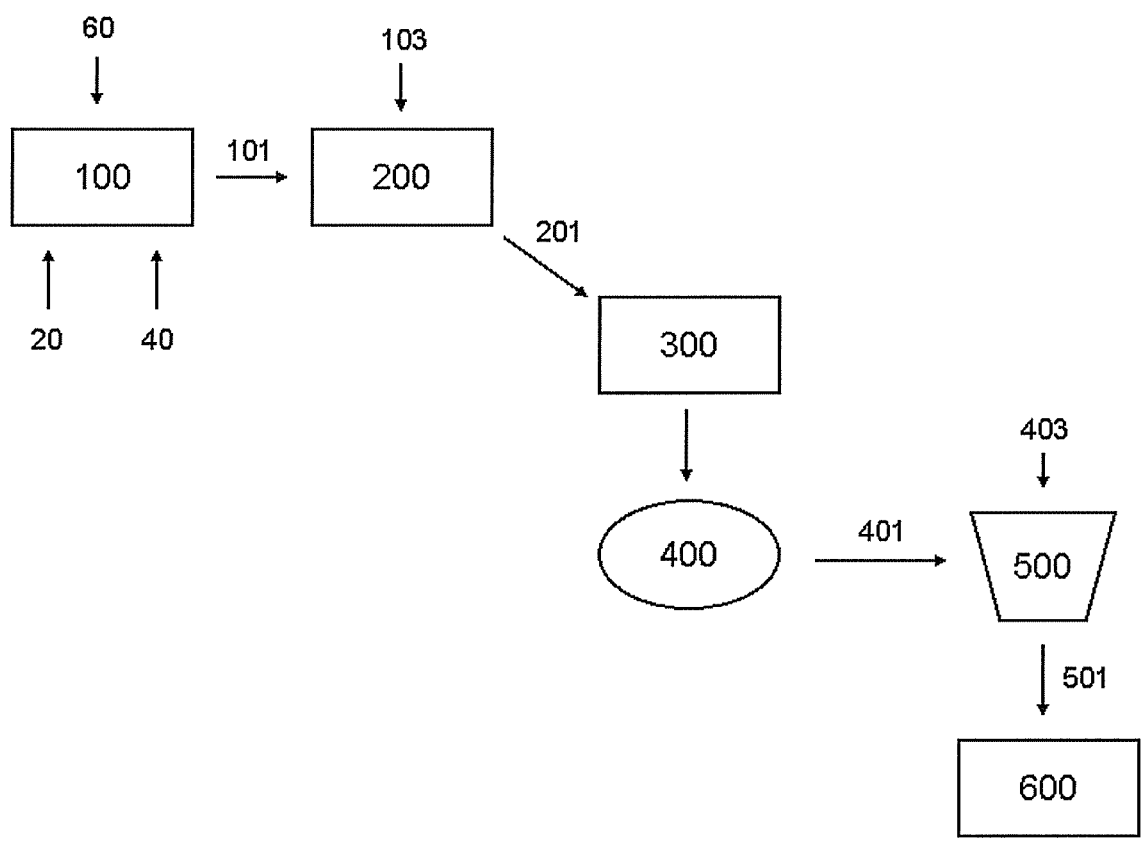

CALCIUM COMPOSITIONS

This application claims the benefit of U.S. provisional application Ser. No. 60/800,178, filed on May 12, 2006, the entire disclosure of which is incorporated herein by reference.

FIELD OF THE INVENTION

The present invention generally relates to pharmaceutical and nutritional compositions comprising calcium carbonate, processes for making such compositions and granulations useful as intermediates in such processes. More specifically, the present invention relates to compositions comprising calcium carbonate having high density and consequently reduced volume for easier swallowing.

BACKGROUND OF THE INVENTION

Calcium is an essential mineral nutrient, needed for formation of strong bones and healthy teeth, and is involved in helping blood to clot. It is also required to transmit nerve signals, and for muscle contraction, heartbeat, glandular secretion and maintenance of immune function. Calcium is found in nutritionally useful amounts in a variety of foods including milk and other dairy products, as well as in green vegetables such as spinach, in nuts and in fish with bones such as sardines. Usually, nutritional requirements for calcium are met from the diet. However, when there is insufficient calcium in the diet to meet the body's needs, supplements are needed to prevent calcium deficiency. Calcium supplements can be of value even where overall dietary intake of calcium is adequate, for example to even out day-to-day or week-to-week variations in intake and provide a "margin of error" in satisfying daily nutritional requirement.

In addition to helping meet dietary requirements, calcium supplementation has pharmaceutical application, for example in preventing or treating osteoporosis that is characterized by loss of normal bone density and by bone fragility. Among various factors, a chronic shortage of dietary calcium is a key factor contributing to osteoporosis development. Thus administration of a calcium supplement can be therapeutically beneficial, for example to prevent or ameliorate osteoporosis-related symptoms.

Calcium supplements may also provide benefits in reducing colonic mucosal proliferation, which in turn can lower risk of colorectal cancer; lowering systolic blood pressure in hypertensive patients; lowering serum cholesterol in some individuals, with attendant benefits such as lowering risk of stroke; ameliorating symptoms of premenstrual syndrome; and in reducing weight gain in subjects who are obese or at risk of obesity. See, for example, *PDR for Nutritional Supplements*, Thomson P D R, Montvale, N.J., pp. 74-79 (2001).

Absorption of calcium in the small intestine depends on the action of 1,25-dihydroxycholecalciferol, a metabolite of vitamin D. For this reason, some calcium supplements include a source of vitamin D such as vitamin $D_2$ (ergocalciferol) or vitamin $D_3$ (cholecalciferol).

Numerous calcium ($Ca^{2+}$) salts are available for oral use as calcium supplements. Among salts that can effectively be used for calcium supplementation, calcium carbonate and calcium phosphate have the highest elemental calcium content (about 40%). Other salts include calcium citrate (about 21% calcium), calcium lactate (about 13% calcium) and calcium gluconate (about 9% calcium). A common adult daily dose for calcium supplementation is 1200 mg, which is typically provided as two tablets each comprising 600 mg calcium, for example in the form of calcium carbonate. A 600 mg calcium dose is provided by about 1500 mg calcium carbonate. The need for such a large amount of calcium carbonate results in a tablet having a large volume that some consumers or patients find difficulty or feel discomfort in ingestion. This in turn can lead to reduced patient compliance. Even a 300 mg calcium tablet (containing about 750 mg calcium carbonate) is uncomfortably large for some people. It is noteworthy that elderly people, one of the subpopulations that are most prone to osteoporosis, often have especial difficulty in swallowing large dosage forms. Therefore, there is a need for a smaller volume calcium composition that is easier to swallow.

Calcium carbonate tablets are generally prepared by first granulating calcium carbonate powder, typically with a binder, and then compressing the resulting granulation. Calcium carbonate powders are available in two main forms, precipitated and ground. Precipitated calcium carbonate, prepared from limestone by recarbonation and precipitation of calcium carbonate from a solution, is often used and is typically preferred in tablet making for its small particle size and good compressibility. However, precipitated calcium carbonate has a high surface area and differs in its surface chemistry from other forms of calcium carbonate. These properties tend to lead to low density granulations that, on compression, produce relatively large volume dosage forms.

Efforts to develop a lower volume calcium supplement dosage form have included use of alternative $Ca^{2+}$ salts such as calcium citrate. For example, U.S. Pat. No. 6,818,228 to Walsdorf et al. mentions a dietary supplement comprising a high bulk density form of calcium citrate.

Ground calcium carbonate tends to have higher bulk density than precipitated calcium carbonate and is sometimes described in the art as "heavy calcium carbonate." However, it poses its own challenges when used to prepare tablets. Haines-Nutt, *J. Pharm. Pharmac.* 28:468-470 (1976) reported that compacts made up from heavy calcium carbonate are weaker and more friable than similar compacts prepared from heavy magnesium carbonate, and speculated that this might result from absence of water of crystallization in calcium carbonate.

U.S. Patent Application Publication No. 2005/0025811 of Levin et al. relates to highly compactable calcium carbonate granulations and methods for preparing such granulations. The granulations are reportedly prepared by mixing calcium carbonate powder and excipients such as maltodextrin and mineral oil in a mixer capable of creating high shear, and then drying the resulting composition, for example in a fluidized bed convection oven. The calcium carbonate powders used include products known to be ground calcium carbonate (e.g., OMYA-Cal™ FG). Particle size of the calcium carbonate is said to have an effect on compactability of the granulation formed; in the broad median particle diameter range of about 0.1 to about 20 µm, a median particle diameter between about 10 and about 12 µm is said to be preferred. Combinations of larger and smaller particle size powders are also said to be useful. Tablets prepared from such granulations are said to have densities about 20% to at least about 35% greater, and to be about 20% to at least about 35% smaller in volume, than commercially available calcium supplement tablets. Specific examples of tablets containing "600 mg calcium carbonate" (600 mg calcium in the form of calcium carbonate may be intended) are reportedly about 20% smaller in volume than CALTRATE® brand 600 mg tablets.

Product labeling for CALTRATE® 600 of Wyeth makes clear that each tablet contains 600 mg calcium, as calcium carbonate (i.e., about 1500 mg calcium carbonate). The tablet also contains an unspecified amount of starch and <2% croscarmellose sodium, magnesium stearate and titanium dioxide. It is further stated that the tablet may contain <2% of glycerin, methylcellulose, polydextrose, polyethylene glycol, polyvinyl alcohol and talc. See http://www.caltrate.com/products/caltrate600_lbl.asp.

Other commercially available calcium supplement tablets can vary from the above in composition. For example, the product label for FINEST NATURAL™ Calcium 500+D caplets sold by Walgreens states that each caplet contains 500 mg calcium as calcium carbonate (i.e., about 1250 mg calcium carbonate), and 125 IU (i.e., about 3 µg) vitamin D as cholecalciferol. Other ingredients listed are croscarmellose sodium, sodium lauryl sulfate, hydroxypropylmethylcellulose (HPMC), titanium dioxide, magnesium stearate, polyethylene glycol and carnauba wax.

There remains a need in the art for alternative calcium carbonate dosage forms having low volume to improve ease of swallowing, yet having acceptably low friability coupled with rapid disintegration and dissolution upon ingestion, and methods to prepare such dosage forms.

SUMMARY OF THE INVENTION

It has now been found that by addition of a small amount of a porosity increasing agent such as polyethylene glycol or a pharmaceutically acceptable hydrophilic surfactant to calcium carbonate powder, a granulation can be prepared having excellent compressibility to provide a calcium carbonate dosage form such as a tablet having high density (for example, at least about 2000 mg/cm$^3$), in spite of the granulation itself having low tapped density (typically not greater than about 1000 mg/cm$^3$). Furthermore, the granulation can be prepared using ground calcium carbonate. Tablets can be prepared from such a granulation without recourse to formulation aids such as starch in amounts that would result in a calcium carbonate content of the tablets of less than about 90% by weight.

Accordingly, there is now provided a granulation comprising about 95% to about 99% by weight calcium carbonate, for example ground calcium carbonate, about 0.5% to about 5% by weight of a binder and about 0.03% to about 3% by weight of a porosity increasing agent.

Without being bound by theory, it is believed that inclusion of polyethylene glycol or a hydrophilic surfactant enhances compressibility by increasing porosity of the granulation; however, it is not ruled out that other mechanisms could be involved. Thus in one embodiment there is provided a granulation comprising about 95% to about 99% by weight calcium carbonate, for example ground calcium carbonate, about 0.5% to about 5% by weight of a binder and about 0.03% to about 3% by weight of polyethylene glycol and/or one or more pharmaceutically acceptable hydrophilic surfactants.

More particular embodiments include a granulation comprising about 97% to about 98% by weight calcium carbonate; about 1.5% to about 3% by weight binder; and about 0.05% to about 0.2% by weight of a porosity increasing agent.

There is also provided a process for preparing a calcium carbonate granulation as described above. The process comprises (a) contacting a calcium carbonate powder, for example ground calcium carbonate, with water, a porosity increasing agent and a binder under sufficient shear to form a homogeneous mix, and (b) drying the mix to provide a granulation.

In one embodiment, the process comprises mixing the water, the porosity increasing agent and the binder to prepare a binder solution which is then contacted with the calcium carbonate powder.

There is further provided a process for preparing a pharmaceutical or nutritional composition comprising calcium carbonate. The process comprises preparing a calcium carbonate granulation as described above; blending the calcium carbonate granulation with one or more excipients to form a compressible blend; and compressing the blend to prepare a pharmaceutical or nutritional composition, for example in a unit dosage form such as a tablet.

There is still further provided a pharmaceutical or nutritional composition comprising about 90% to about 99% by weight calcium carbonate, about 0.03% to about 3% by weight of a porosity increasing agent, and about 1% to about 10% by weight of other excipients. Density of such a composition can be, without limitation, at least about 2000 mg/cm$^3$ and can be as high as about 2300 mg/cm$^3$ or even higher. The combination of high calcium carbonate load (at least about 90% by weight) and high density (at least about 2000 mg/cm$^3$) enables a tablet composition of the invention containing about 600 mg calcium to have a volume of less than about 0.83 cm$^3$.

An illustrative pharmaceutical composition comprises at least about 95% by weight calcium carbonate and has a density of about 2100 to about 2200 mg/cm$^3$.

In one embodiment, the pharmaceutical composition is in tablet form and comprises about 600 mg calcium. In another embodiment, the pharmaceutical composition is in tablet form, comprises about 600 mg calcium and has a volume of less than about 0.76 cm$^3$.

There is still further provided a method for supplementing calcium nutrition in a subject, comprising administering to the subject a composition comprising about 90% to about 99% by weight calcium carbonate, about 0.03% to about 3% by weight of a porosity increasing agent, and about 1% to about 10% by weight of other excipients, in an amount providing about 300 to about 1200 mg calcium per day.

There is still further provided a method for treating or reducing risk of a medical disorder associated with calcium deficiency and/or hypocalcemia in a subject, comprising administering to the subject a composition comprising about 90% to about 99% by weight calcium carbonate, about 0.03% to about 3% by weight of a porosity increasing agent, and about 1% to about 10% by weight of other excipients, in an amount providing about 300 to about 1200 mg calcium per day.

These and other embodiments are more fully described in the detailed description that follows.

BRIEF DESCRIPTION OF THE DRAWING

The drawing described herein is for illustration purposes only and is not intended to limit the scope of the present disclosure in any way.

FIG. 1 is a process flow diagram illustrating one embodiment of a manufacturing process for making a calcium supplement composition of the present invention.

It should be understood that throughout the drawing, corresponding reference numerals indicate like or corresponding parts and features.

DETAILED DESCRIPTION

The following description is merely exemplary in nature and is not intended to limit the present disclosure, application, or uses.

In accordance with the present invention, improved processes for preparing calcium carbonate granulations have been discovered that permit using ground calcium carbonate. Without being bound by a particular theory, it has been discovered that addition of a porosity increasing agent to ground calcium carbonate, for example addition to a binder solution used with ground calcium carbonate, results in granulations having increased granule porosity and better compactability as compared to conventional calcium carbonate granulations. The granulations of the present invention further allow for preparation of calcium dosage forms having a lower volume, resulting from significantly higher density and/or from higher calcium carbonate loading due to lower content of excipients. This lower volume in turn allows for formulation of smaller dosage forms that are easier to swallow and/or the formulation of calcium carbonate with other nutrients or active ingredients without significantly varying from standard dosage form volumes. Lower volume also permits savings in packaging and shipping costs.

Importantly, although compressed dosage forms such as tablets prepared from the present granulations typically have high density (for example at least about 2000 mg/cm$^3$), it has further been discovered that these dosage forms exhibit acceptably low friability, and have excellent disintegration and dissolution properties, as illustrated in the Examples herein.

A first embodiment of the invention provides a calcium carbonate granulation. The term "granulation" herein, when applied to a composition as opposed to a process step, refers to an intermediate useful in preparing a compressed dosage form such as a tablet. A granulation typically is a free-flowing granular material comprising more or less discrete secondary particles that themselves comprise aggregates of smaller primary particles. Thus a calcium carbonate granulation comprises secondary particles, illustratively of volume mean diameter about 100 to about 500 μm, which in turn comprise primary calcium carbonate particles, illustratively of volume mean diameter about 12 to about 22 μm. Various processes are known in the art for preparing granulations, including wet granulation, dry granulation, fluidized bed granulation and extrusion granulation; in a particular embodiment, calcium carbonate granulations are prepared by a wet granulation process as described in greater detail hereinbelow.

As indicated above, a granulation of the present invention comprises about 95% to about 99% by weight calcium carbonate, about 0.5% to about 5% by weight of a binder and about 0.03% to about 3% by weight of a porosity increasing agent. All weights herein are expressed on a dry basis (i.e., excluding any moisture that may be present in a composition) unless the context demands otherwise.

Any particulate form, or combination of forms, of calcium carbonate can be used, including ground calcium carbonate. Particle size of the calcium carbonate is not critical within a wide range, for example from about 0.1 to about 30 μm, expressed as volume mean diameter, although processing considerations (as indicated hereinbelow) may favor selection of a calcium carbonate powder having a volume mean diameter of about 10 to about 25 μm, for example about 12 to about 22 μm. In various embodiments, the granulation comprises at least about 96% or at least about 97% by weight calcium carbonate. In a particular embodiment, the granulation comprises about 97% to about 98% by weight calcium carbonate. Amounts of calcium carbonate as expressed herein are inclusive of natural impurities present in the calcium carbonate source. Calcium carbonate sources of high natural purity, for example conforming to pharmacopeial standards such as USP (United States Pharmacopeia), are generally preferred. In the case of ground calcium carbonate, such sources include the mineral calcite.

Importantly according to the present invention, the granulation comprises a porosity increasing agent, which can comprise a single material or a combination of two or more materials. Porosity increasing agents useful herein are hydrophilic and include polyethylene glycols of a range of molecular weights, and a variety of pharmaceutically acceptable hydrophilic surfactants, which can be nonionic or anionic. Suitable hydrophilic surfactants include without limitation sorbitan fatty acid esters such as sorbitan monopalmitate or sorbitan monolaurate; polyoxyethylene sorbitan fatty acid esters such as polyoxyethylene 4 sorbitan monostearate, polyoxyethylene 20 sorbitan tristearate, polyoxyethylene 5 sorbitan monooleate, polyoxyethylene 20 sorbitan monooleate (polysorbate 80) or polyoxyethylene 20 sorbitan trioleate; alkyl sulfates such as sodium lauryl sulfate; sulfosuccinates such as docusate sodium, docusate potassium or docusate calcium; glyceryl fatty acid esters such as glyceryl monostearate; polyglycol fatty acid esters, more particularly polyoxyethylene fatty acid esters and propylene glycol fatty acid esters such as propylene glycol monolaurate; poloxamers such as poloxamer 188 or poloxamer 407; polyoxyethylene castor oil derivatives and combinations thereof.

In a preferred embodiment the porosity increasing agent comprises polyethylene glycol, polysorbate 80, docusate sodium, sodium lauryl sulfate or a combination thereof.

The porosity increasing agent is present in the granulation in an amount of about 0.03% to about 3% by weight, more typically about 0.04% to about 1% or about 0.05% to about 0.5%, for example about 0.05% to about 0.2% by weight.

Any binder known in the art can be used, including povidone of any suitable K-value; copovidone; modified celluloses such as HPMC, hydroxypropylcellulose, carmellose sodium or a combination thereof. In a preferred embodiment, the binder comprises povidone, for example povidone K-90. In various embodiments the binder is present in the granulation in an amount of about 0.5% to about 5%, about 0.4% to about 4%, about 1% to about 3.5%, or about 1.5% to about 3%, by weight.

Other ingredients can be present in the granulation if desired.

The granulation should be free-flowing and is typically of a sand-like texture. Particle size (i.e., secondary particle size) distribution is not narrowly critical, but, illustratively, less than about 2% by weight of the granulation is retained by a 20 mesh sieve, about 30% to about 42% by weight of the granulation is retained by a 60 mesh sieve, about 55% to about 70% of the granulation is retained by a 100 mesh sieve, and at least about 80% by weight of the granulation is retained by a 200 mesh sieve. All mesh sizes herein refer to Tyler Standard sieve series, using a Tyler Ro-Tap sieve shaker for particle size analysis. Put another way, in one embodiment at least about 30% by weight of the particles are larger than about 250 μm, at least about 55% by weight of the particles are larger than about 150 μm, and at least about 80% by weight of the particles are larger than about 75 μm.

To be useful in preparing a high density tablet, it is generally suggested in the art that a relatively high density granulation is desirable. For example, according to above-cited U.S. Patent Application Publication No. 2005/0025811 ("the '811 publication"), at paragraph 0015 thereof: "Preferred granulated calcium carbonate compositions are provided having an average tap density between about 1.1 and about 2.0 g/cm$^3$. The most preferred granulated calcium carbonate compositions according to the invention have tap densities greater than 1.3 g/cm$^3$."

The present invention, contrary to the '811 publication, provides a granulation that typically has relatively low tapped density. In one embodiment, the tapped density (1000 taps) of a granulation as described above is less than about 1100 mg/cm$^3$, for example about 750 to about 1050 mg/cm$^3$, more typically about 800 to about 1000 mg/cm$^3$. This is a considerably lower density than a typical ground calcium carbonate powder used as a starting material, which can illustratively have a tapped density (1000 taps) of about 1400 to about 1700 mg/cm$^3$. It is believed, again without being bound by theory, that incorporation of a porosity increasing agent in the granulation in accordance with the present invention accounts for the unusually low tapped density of the granulation. Yet, in spite of the low density of the granulation, it is capable of compaction to provide a tablet having higher density than commercially available calcium carbonate tablets, as demonstrated hereinbelow. It is further believed, again without being bound by theory, that the porosity increasing agent leads to creation of channel structures in the granulation, and that drying and then compacting the granulation results in a collapsing of the channel structures to form a highly packed composite providing tablets with high density and low volume.

The granulations of the present invention are not limited by the process used to prepare them. An illustrative process for preparing a granulation as described above is now described.

In the illustrative process, a calcium carbonate powder, for example ground calcium carbonate, is first contacted with water, a porosity increasing agent and a binder, under sufficient shear to provide a homogeneous mix. Suitable calcium carbonate sources for use in the process generally include any calcite form of calcium carbonate having a volume mean particle size of about 12 to about 22 μm and a bulk density of about 900 to about 1100 mg/cm³. In a preferred embodiment, the calcium carbonate source is a calcite form of calcium carbonate having a volume mean particle size of about 16 to about 18 μm, an overall surface energy of at least about 35 mJ/m², a surface polarity of at least about 30%, and a tapped density (1000 taps) of about 1400 to about 1700 mg/cm³. Suitable porosity increasing agents and binders are as described above. Relative amounts of calcium carbonate, porosity increasing agent and binder are as set forth above; for the present process about 97 to about 98 parts by weight calcium carbonate, about 0.05 to about 0.2 parts by weight porosity increasing agent and about 1.5 to about 3 parts by weight binder will generally be found suitable. A suitable amount of water to provide satisfactory granulation will be readily determined by one of skill in the art by routine experimentation; typically such an amount will be about 10% to about 15%, for example about 11% to about 14%, of the weight of the calcium carbonate.

In a particular embodiment, the water, porosity increasing agent and binder are first mixed to prepare a binder solution, which is then contacted with the calcium carbonate. A suitable binder solution generally comprises about 10% to about 20% by weight of the binder, about 0.2% to about 1.5% (for example about 0.3% to about 1.3%) by weight of the porosity increasing agent, and about 80% to about 90% by weight water.

A binder solution can be prepared by contacting the binder and the porosity increasing agent with water while mixing. Illustratively, the binder is introduced into a vessel with water heated to a temperature of about 25° C. to about 40° C., and mixed at a mixing speed of about 2000 to about 8000 rpm until the binder is dissolved. After the binder is dissolved, the mixing speed is reduced and the porosity increasing agent is added slowly. A reduced mixing speed of about 2000 to about 3000 rpm is maintained until the porosity increasing agent is adequately dispersed.

The water, porosity increasing agent and binder (or, in the particular embodiment described above, the solution containing the binder and porosity increasing agent) are added to the calcium carbonate under shear conditions sufficient to provide a homogeneous mix, or "wet granulation composition". In a particular embodiment, the binder solution and calcium carbonate are contacted in a continuous high shear paddle mixer operating at an impeller speed of about 1800 to about 2000 rpm. The calcium carbonate is introduced into the mixer at a rate of about 1700 to about 1900 g/minute. The binder solution is introduced into the mixer at a rate of about 245 to about 350 g/minute. The amount of binder solution is controlled to give a granulation moisture level of about 11% to about 14% based on the amount of calcium carbonate used.

The resulting wet granulation composition is dried, for example in a fluidized bed or tray dryer at a temperature of about 40° C. to about 60° C. to provide a granulation of the invention. The composition is dried to a moisture level of not greater than about 2% by weight, preferably from about 0.3% to about 1% by weight. The dried granulation is then optionally screened, for example using an 18 to 20 mesh screen, to remove any oversized particles.

After drying, the granulation prepared as above comprises at least about 97% by weight calcium carbonate, about 1.5% to about 3% by weight binder and about 0.01% to about 0.2% by weight porosity increasing agent, and has a moisture content of less than about 2% by weight. In a particular embodiment, the granulation comprises about 97% to about 98% by weight calcium carbonate, about 1.8% to about 2.9% by weight binder and about 0.05% to about 0.15% by weight porosity increasing agent, and has a moisture content of about 0.3% to about 1% by weight after drying. In a further particular embodiment, the dry granulation comprises 97.5% ground calcium carbonate, 2.4% povidone K-90 and 0.1% polysorbate 80.

Granulations prepared as above typically have a tapped density (1000 taps) of about 800 to about 1000 mg/cm³.

Referring now to FIG. 1, one embodiment of a process of the present invention for preparing a calcium granulation is illustrated schematically. The process generally comprises contacting water 20, a binder 40 and a porosity increasing agent 60 in a mixer 100 to prepare a binder solution 101. The binder solution 101 is then contacted with calcium carbonate 103 in a continuous high shear paddle mixer 200 to prepare a wet granulation composition 201. The wet granulation composition 201 is dried in a fluidized bed or tray dryer 300, then screened with a screen or sieve 400 to remove any oversized particles and provide the finished granulation 401.

The resulting granulation can be used for filling capsules, or can be processed into tablets or other types of solid unit dosage forms. The granulation is especially useful in preparation of compressed unit dosage forms such as tablets for oral administration as nutritional supplements or medicaments. Granulations of the present invention, in spite of having relatively low tapped density, are compressible to form high density tablets.

Thus, a further embodiment of the invention provides a process for preparing a pharmaceutical or nutritional composition comprising calcium carbonate. The process comprises preparing a calcium carbonate granulation, for example as described above; blending the calcium carbonate granulation with one or more excipients to form a compressible blend; and compressing the blend to prepare a pharmaceutical or nutritional composition, for example in a unit dosage form such as a tablet. In one embodiment, the total amount of such excipients and any other materials added to the blend is sufficiently small that the resulting composition, for example tablet, comprises at least about 90% by weight, for example about 90% to about 99% by weight, calcium carbonate. In practice this means, for example, if the granulation contains about 97% by weight calcium carbonate, no more than about 7% by weight of excipients and other ingredients should be added to the blend in preparing the tableting mix.

Referring again to FIG. 1, the dry granulation 401 is, in one embodiment, contacted with one or more excipients 403 including, for example, diluents or fillers, disintegrants or disintegrating agents, wetting agents, anti-adherents, glidants, lubricants, and/or other miscellaneous adjuncts such as colorants, and optionally with one or more additional nutritional or pharmaceutically active ingredients, for example vitamins such as vitamin D, in a blender 500 to form a tableting mix 501 which is then compressed into tablets with a tablet press 600.

Diluents such as starch or lactose are typically not required in preparing tablets according to the present invention, but small amounts, for example amounts that do not dilute calcium carbonate content of the tablets below about 90%, can be added if desired.

One or more disintegrants can be included to assist breaking up of the tablet in the gastrointestinal tract after swallowing, and thereby accelerate dissolution to release calcium for intestinal absorption. Disintegrants can be generally be incorporated into the granulation (intragranular disintegrant) during the granulation process, or into the tableting mix prior to compression (extragranular disintegrant), or both. Examples of suitable disintegrants that can be used are starch, sodium starch glycolate, alginic acid, guar gum, croscarmellose sodium, crospovidone, ion exchange resins and combinations thereof. Tablets can illustratively contain about 1% to about 5%, for example about 1.5% to about 4% or about 2% to about 3%, by weight in total of one or more disintegrants, for example crospovidone, sodium starch glycolate and/or croscarmellose sodium.

One or more wetting agents can be included if desired, for example to assist in dispersion of the calcium carbonate in gastrointestinal fluid and thereby further accelerate dissolution. Wetting agents, if used, can be the same as or different from hydrophilic surfactants used in the granulation process as porosity increasing agents. For example, sodium lauryl sulfate is a useful wetting agent. Illustratively about 0.05% to about 0.5%, for example about 0.1% to about 0.25%, by weight of one or more wetting agents can optionally be added to the tableting mix.

Materials useful to improve flow characteristics of granulations, for example in preparing a tableting mix, are referred to as glidants. Suitable glidants include, for example, silicon dioxide, magnesium lauryl sulfate, magnesium aluminum silicate, magnesium oxide, talc, clays and combinations thereof. Glidants can be blended with the granulation to reduce inter-particulate friction and to eliminate problems associated with the flow of the tableting mix from larger to smaller apertures in a tablet press.

Lubricants may also be added to reduce friction and wear during processing. Some lubricants also demonstrate anti-adherent properties that can prevent the tableting mix from sticking during the tablet making process. Examples of suitable lubricants include magnesium stearate, talc, stearic acid, sodium stearyl fumarate, hydrogenated vegetable oil, high melting point waxes and combinations thereof.

Tablets can illustratively contain about 0.1% to about 2%, for example about 0.25% to about 1%, by weight in total of one or more glidants, lubricants and/or anti-adherents.

As indicated above, the relatively low density granulations of the invention can be compressed to form high density tablets having a high loading (at least about 90% by weight) of calcium carbonate. To achieve this, a compression force should be applied that is sufficient, in the particular tablet press fitted with the particular tablet dies to be used, to compress the tableting mix into a tablet having a density of at least about 2000 mg/cm$^3$. One of ordinary skill in the art is able, by routine experimentation, to establish a suitable compression force for any particular tablet composition using any particular tableting equipment. Tablet density can be as high as about 2300 mg/cm$^3$ or even higher; however, it is generally desirable to avoid excessively high tablet densities as these can lead to difficulties in disintegration and dissolution. In addition, tablets compressed with excessive force can be excessively friable, and consequently do not stand up well to mechanical stresses during manufacture, packaging and shipping. In a particular embodiment, a compression force is selected to provide a tablet density of about 2100 to about 2200 mg/cm$^3$.

Yet another embodiment of the invention provides a pharmaceutical or nutritional composition comprising about 90% to about 99% by weight calcium carbonate, about 0.03% to about 3% by weight of a porosity increasing agent, and about 1% to about 10% by weight of other excipients, including about 0.5% to about 5% by weight of binder present in the granulation before blending. Density of such a composition can be, without limitation, at least about 2000 mg/cm$^3$ and can be as high as about 2300 mg/cm$^3$ or even higher.

As referred to herein, the amount by weight of porosity increasing agent in a pharmaceutical or nutritional composition includes, for convenience, not only the amount added in the granulation process as described above, but also any amount of polyethylene glycol or hydrophilic surfactant optionally added as an excipient (e.g., as a wetting agent) to the tableting mix prior to compression.

In a preferred embodiment, the composition is a unit dosage form, in particular a compressed unit dosage form such as a tablet. "Tablets" herein embrace compressed dosage forms of any shape, including those elongated forms referred to in the art as "caplets". In various embodiments, a tablet of the invention can comprise about 92% to about 98%, for example about 94% to about 97%, by weight calcium carbonate. An illustrative pharmaceutical composition comprises at least about 95% by weight calcium carbonate and has a density of about 2100 to about 2200 mg/cm$^3$.

Tablets can be made in any desired size and shape but it is preferred that tablet volume is no greater than about 0.83 cm$^3$. It can be calculated that a tablet having at least about 90% by weight calcium carbonate, and having a density of at least about 2000 mg/cm$^3$ and a volume no greater than about 0.83 cm$^3$, can contain 600 mg calcium.

Unit dosage forms of the invention illustratively contain about 300 to about 600 mg calcium, in the form of calcium carbonate. In one embodiment, the pharmaceutical or nutritional composition is in tablet form and comprises about 600 mg calcium.

The combination of high calcium carbonate load (at least about 90% by weight) and high density (at least about 2000 mg/cm$^3$) enables a tablet composition of the invention containing about 600 mg calcium to have a volume of less than about 0.83 cm$^3$. The volume of such a tablet, in some embodiments, is about 0.67 to about 0.83 cm$^3$, for example about 0.7 to about 0.8 cm$^3$ or about 0.72 to about 0.77 cm$^3$. Lower dose tablets, containing for example about 550 mg, about 500 mg, about 450 mg, about 400 mg, about 350 mg or about 300 mg calcium, can have proportionally lower volume.

For comparison, commercially available CALTRATE® 600 mg calcium tablets of Wyeth have been determined to have an average weight of about 1850 mg; based on a calcium carbonate amount of about 1500 mg (equivalent to 600 mg calcium) and assuming a moisture content of about 0.5%, the calcium carbonate loading of these tablets is calculated to be about 81.5% by weight. These tablets have further been determined to have a density of about 1950 mg/cm$^3$ and an average volume of about 0.95 cm$^3$.

In a particular embodiment of the present invention, the pharmaceutical or nutritional composition is in tablet form, comprises about 600 mg calcium and has a volume of less than about 0.76 cm$^3$, for example about 0.72 to about 0.76 cm$^3$.

Thus, the present invention allows for the preparation of tablets comprising about 300 to about 600 mg calcium in the form of calcium carbonate, and having a volume that is about 15% to about 30% smaller than conventional calcium carbonate tablets such as CALTRATE® tablets.

Tablets prepared from the granulations of the present invention illustratively exhibit a breaking force of about 25 to about 30 Kp, a tablet density of from about 2100 to about 2200 mg/cm$^3$, a friability of about 0.1% to about 0.4%, and a disintegration time of about 4 to about 8 minutes, all as measured using tests standard in the art. A 600 mg calcium tablet of the invention illustratively has a thickness of about 0.26 to about 0.27 inches (about 6.7 to about 6.9 mm) and a tablet weight of about 1540 to about 1640 mg.

Pharmaceutical and nutritional compositions of the invention optionally further comprise one or more additional pharmaceutically or nutritionally active ingredients. In some embodiments, such additional ingredients comprise one or more vitamins or vitamin sources. In a particular embodiment, a composition of the invention comprises a vitamin D source such as vitamin $D_2$ (ergocalciferol) or vitamin $D_3$ (cholecalciferol), which can enhance intestinal absorption of calcium. Such additional ingredients can be added at any stage in the process of preparing a composition, including the granulation process, but typically it will be found most convenient to add such ingredients after granulation, when preparing a blend for example as a tableting mix. Some vitamins such as vitamin D are used in very small quantities and it can be advantageous to add them to the tableting mix in the form of dilute solutions in a suitable solvent, for example vegetable oil, polysorbate 80 or propylene glycol in the case of vitamin $D_3$, or as a powder in mixture with a solid diluent such as sucrose, starch and/or dextrin.

In one embodiment, a calcium carbonate tablet of the invention, for example as described in detail above, comprising about 300 to about 600 mg calcium in the form of calcium carbonate, further comprises a vitamin D source, illustratively vitamin $D_3$, in an amount of about 1 to about 30 μg, for example about 2.5 to about 25 μg, about 3 to about 20 μg or about 5 to about 15 μg per tablet, wherein 1 μg is equivalent to 40 IU vitamin D.

A nutritional composition of the invention is useful in a method for supplementing calcium nutrition in a subject, the method comprising administering to the subject such a composition, for example one or more tablets, in an amount providing about 300 to about 1500 mg calcium per day, for example about 600 to about 1200 mg calcium per day.

Calcium supplementation is advantageous not only where the diet is low in calcium, but also where hypocalcemia is caused or exacerbated by other factors. For example, calcium absorption into the circulatory system can be decreased by low levels of parathyroid hormone secretion (hypoparathyroidism), e.g., post-operative, autoimmune or congenital hypoparathyroidism, or reduced response to parathyroid hormone secretion (pseudohypoparathyroidism); magnesium depletion or extreme hypermagnesemia; or vitamin D deficiency. Calcium loss from the circulatory system can be increased by hyperphosphatemia, for example associated with renal failure, rhabdomyolysis, tumor lysis or phosphate administration; acute pancreatitis; chelating agents such as citrate, lactate or EDTA; or osteoblastic metastases, for example in prostate or breast cancer. Other causal factors for hypocalcemia can include sepsis, excessive fluoride intake or surgery.

Calcium absorption can be reduced or calcium loss increased as a side effect of certain drugs such as steroids (including steroidal hormones such as estrogen), proton pump inhibitors (PPIs), certain antivirals such as foscarnet, or certain chemotherapeutics such as cisplatin, 5-fluorouracil or leucovorin. Thus in one embodiment, a composition of the invention is administered concomitantly with a drug such as a steroid, PPI antiviral or chemotherapeutic that reduces calcium absorption or increases calcium loss, the composition being administered in an amount effective to at least partly offset the reduced calcium absorption or increased calcium loss.

A pharmaceutical composition of the invention is useful in a method for treating or reducing risk of a medical disorder precipitated or aggravated by calcium deficiency and/or hypocalcemia in a subject, the method comprising administering to the subject such a composition, for example one or more tablets, in an amount providing about 300 to about 1500 mg calcium per day, for example about 600 to about 1200 mg calcium per day.

Examples of medical disorders that can be precipitated or aggravated by calcium deficiency, particularly chronic calcium deficiency, and/or hypocalcemia include without restriction bone disorders including osteoporosis, osteomalacia and rickets; joint disorders; periodontal disorders; prostate or colorectal cancer; hypertension, for example systolic hypertension; kidney stones (due, for example, to excess calcium in urine associated with depletion of bone calcium); hyperlipidemia; cardiovascular and/or hemorrhagic disorders including stroke; menstrual disorders including premenstrual syndrome; miscarriage; birth, particularly heart, defects; obesity; sleep disorders; and mental, for example depressive, disorders.

In one embodiment, a composition of the invention is administered concomitantly with a drug that treats or alleviates a medical disorder precipitated or aggravated by calcium deficiency and/or hypocalcemia.

EXAMPLES

The following examples are merely illustrative, and do not limit this disclosure in any way.

Example 1

This example describes the preparation of a dry granulation comprising ground calcium carbonate, a binder and a porosity increasing agent.

The granulation was prepared in general accordance with the process illustrated in FIG. 1 and described above. The experiment was begun by preparing a binder solution in a stainless steel mixer. The solution was prepared by adding heated water (263.75 g/min at 30° C. to 35° C.) to the vessel followed by binder (povidone K-90, 44.3 g/min). The binder was mixed at an impeller speed of about 7200 rpm until dissolved. Once the binder was dissolved, the mixing speed was reduced to about 2200 rpm and the porosity increasing agent (polysorbate 80, 1.85 g/min) was added slowly and mixed until dispersed. Mixing was continued for approximately 10 minutes to ensure that the porosity increasing agent was adequately dispersed. The resulting binder solution comprised 85.1% water, 14.3% binder and 0.6% porosity increasing agent.

The binder solution and calcium carbonate were then introduced into a continuous high shear paddle mixer (Turbulizer, Model TCS, Size 8 commercially available from Hosakawa Bepex, Minneapolis, Minn.) to produce a calcium carbonate granulation. The ground calcium carbonate (Calcipure™ calcium carbonate HD 212 USP/Ph. Eur., Code 9-4863) was fed into the continuous high shear paddle mixer at a controlled rate (1800 g/min) using a powder feeder (AccuRate Model No. 580-354600). The binder solution was introduced to the continuous high shear paddle mixer at a controlled rate (309.9 g/min) by means of a progressing cavity pump and spray nozzle. The mixer was operated continuously with an impeller speed of about 1900 rpm until the desired amount of granulation was produced. The material exiting the continuous high shear paddle mixer was continually monitored visually and evaluated for texture and moisture. The finished granulation was dried at approximately 45° C. to a moisture level of no more than 2% by weight. The resulting dried material was passed through an oscillator using a 20 mesh screen to remove any oversized particles.

The final dry granulation contained 97.5% ground calcium carbonate, 2.4% binder and 0.1% porosity increasing agent. The granulation exhibited a typical tapped density (1000 taps) of 0.9 g/ml. The granulation had a typical particle size (determined using a Tyler Ro-tap sieve shaker) as shown in Table 1.

TABLE 1

| U.S. Std. Sieve | Cum. % Retained |
| --- | --- |
| 20 | 0% |
| 60 | 39% |
| 100 | 67% |
| 200 | 89% |

Example 2

This example describes the preparation of tablets comprising 600 mg calcium using the granulation described in Example 1.

The tablets were prepared by blending the calcium carbonate granulation prepared in Example 1 with crospovidone (20.6 mg/tablet), sodium starch glycolate (20.6 mg/tablet), magnesium stearate (7.91 mg/tablet) and sodium lauryl sulfate (3.17 mg/tablet) in a P-K twin shell blender. The total theoretical tablet weight was 1590.7 mg comprising 96.71% of the calcium carbonate granulation, 1.29% crospovidone, 1.29% sodium starch glycolate, 0.5% magnesium stearate and 0.2% sodium lauryl sulfate. Tablets were produced from the blend using 0.3125 inch×0.7500 inch (approximately 7.5 mm×18 mm) modified capsule shaped tooling at a compression force of approximately 42 kN. The tablets exhibited excellent tablet characteristics including high breaking force, low friability, low volume, high density, short disintegration time and fast dissolution rate, as shown in Table 2.

TABLE 2

| Breaking force (Kp) | Tablet thickness (mm) | Tablet wt. (mg) | Tablet vol. (cm$^3$) | Tablet density (mg/cm$^3$) | Friability (100 drops) (%) | Disint. time (min) | Dissolution (30 min) (%) |
|---|---|---|---|---|---|---|---|
| 27.5 | 6.4 | 1592 | 0.732 | 2174.9 | 0.13 | 4.0 | 95 |

Example 3

This example describes the preparation of tablets comprising 600 mg calcium with vitamin D$_3$ using the granulation described in Example 1.

The tablets were prepared by blending the calcium carbonate granulation produced in Example 1 (1538.54 mg/tablet) with vitamin D$_3$ (1.11 mg/tablet of a vitamin D$_3$ powder containing 400 IU/mg, i.e., 11 μg vitamin D$_3$/tablet), croscarmellose sodium (39.56 mg/tablet), stearic acid (3.97 mg/tablet), magnesium stearate (3.97 mg/tablet) and sodium lauryl sulfate (1.59 mg/tablet) in a P-K twin shell blender. The total theoretical tablet weight was 1588.7 mg, comprising 96.84% of the calcium carbonate granulation, 0.07% vitamin D$_3$ solution, 2.49% croscarmellose sodium, 0.25% stearic acid, 0.25% magnesium stearate and 0.1% sodium lauryl sulfate. Tablets were produced from the blend using 0.3125 inch× 0.7500 inch (approximately 7.5 mm×18 mm) modified capsule shaped tooling at a compression force of approximately 42 kN. The tablets exhibited excellent tablet characteristics including high breaking force, low friability, low volume, high density, short disintegration time and fast dissolution rate, as shown in Table 3.

TABLE 3

| Breaking force (Kp) | Tablet thickness (mm) | Tablet wt. (mg) | Tablet vol. (cm$^3$) | Tablet density (mg/cm$^3$) | Friability (100 drops) (%) | Disint. time (min) | Dissolution (30 min) (%) |
|---|---|---|---|---|---|---|---|
| 24.8 | 6.4 | 1592 | 0.735 | 2166.0 | 0.25 | 4.0 | 98 |

All patents and publications cited herein are incorporated by reference into this application in their entirety.

The words "comprise", "comprises", and "comprising" are to be interpreted inclusively rather than exclusively.

What is claimed is:

1. A granulation comprising about 95% to about 99% by weight calcium carbonate, about 0.5% to about 5% by weight of a binder and about 0.03% to about 3% by weight of a porosity increasing agent selected from the group consisting of polyethylene glycol, sorbitan fatty acid esters, polyoxyethylene sorbitan fatty acid esters, alkyl sulfates, sulfosuccinates, glyceryl fatty acid esters, polyglycol fatty acid esters, poloxamers, polyoxyethylene castor oil derivatives and combinations thereof, wherein the calcium carbonate is derived from a calcite form of calcium carbonate having a tapped density (1000 taps) of about 1400 to about 1700 mg/cm$^3$ and the granulation has a tapped density (1000 taps) of about 800 to about 1000 mg/cm$^3$.

2. The granulation of claim 1, wherein the calcium carbonate comprises ground calcium carbonate.

3. The granulation of claim 2, wherein the ground calcium carbonate has a volume mean particle size of about 12 to about 22 μm.

4. The granulation of claim 1, wherein the porosity increasing agent comprises polyethylene glycol.

5. The granulation of claim 1, wherein the porosity increasing agent is selected from the group consisting of sorbitan fatty acid esters, polyoxyethylene sorbitan fatty acid esters, alkyl sulfates, sulfosuccinates, glyceryl fatty acid esters, polyglycol fatty acid esters, poloxamers, polyoxyethylene castor oil derivatives and combinations thereof.

6. The granulation of claim 1, wherein the porosity increasing agent comprises polysorbate 80, docusate sodium, sodium lauryl sulfate or a combination thereof.

7. The granulation of claim 1, comprising (a) about 97% to about 98% by weight calcium carbonate; (b) about 1.5% to about 3% by weight of a binder; and (c) about 0.05% to about 0.2% by weight of a porosity increasing agent.

8. The granulation of claim 1, wherein the binder comprises at least one agent selected from the group consisting of povidone, copovidone, hydroxypropylcellulose, hydroxypropylmethylcellulose, carmellose sodium and combinations thereof.

9. The granulation of claim 1, wherein the binder comprises povidone.

10. The granulation of claim 1, having a particle size distribution such that less than about 2% by weight of the granulation is retained by a 20 mesh sieve, about 30% to about 42% by weight of the granulation is retained by a 60 mesh sieve, about 55% to about 70% of the granulation is retained by a 100 mesh sieve, and at least about 80% by weight of the granulation is retained by a 200 mesh sieve.

11. A pharmaceutical or nutritional composition comprising the granulation of claim 1 and at least one extragranular excipient, wherein the composition comprises at least about 90% by weight calcium carbonate.

12. A pharmaceutical or nutritional composition comprising about 90% to about 99% by weight calcium carbonate, wherein the composition comprises:
(a) a granulation comprising about 95% to about 99% by weight calcium carbonate, about 0.5% to about 5% by weight of a binder, about 0.03% to about 3% by weight of a porosity increasing agent selected from the group consisting of polyethylene glycol, sorbitan fatty acid esters, polyoxyethylene sorbitan fatty acid esters, alkyl sulfates, sulfosuccinates, glyceryl fatty acid esters, polyglycol fatty acid esters, poloxamers, polyoxyethylene castor oil derivatives and combinations thereof, wherein the granulation has a tapped density (1000 taps) of about 800 to about 1000 mg/cm$^3$; and (b) about 1% to about 10% by weight of other excipients; wherein the composition is in the form of a tablet having a density of about 2000 to about 2300 mg/cm$^3$ and a volume of less than about 0.83 cm$^3$.

13. The composition of claim 12, comprising about 300 to about 600 mg calcium.

14. The composition of claim 13, wherein the tablet comprises at least about 93% by weight calcium carbonate.

15. The composition of claim 13, having a density of about 2100 to about 2200 mg/cm$^3$.

16. The composition of claim 15, wherein the tablet comprises at least about 95% by weight calcium carbonate.

17. The composition of claim 12, the composition comprising about 600 mg calcium.

18. The composition of claim 12 comprising about 600 mg calcium, having a density of about 2100 to about 2200 mg/cm$^3$, and having a volume of less than about 0.76 cm$^3$.

19. The composition of claim 12 further comprising a vitamin D source in an amount of about 1 to about 30 μg vitamin D per unit dosage form.

20. The composition of claim 19, wherein the vitamin D source comprises vitamin D$_3$.

21. The composition of claim 12, wherein the porosity increasing agent comprises polyethylene glycol.

22. The composition of claim 12, wherein the porosity increasing agent is selected from the group consisting of sorbitan fatty acid esters, polyoxyethylene sorbitan fatty acid esters, alkyl sulfates, sulfosuccinates, glyceryl fatty acid esters, polyglycol fatty acid esters, poloxamers, polyoxyethylene castor oil derivatives and combinations thereof.

23. The composition of claim 12, wherein the porosity increasing agent comprises polysorbate 80, docusate sodium, sodium lauryl sulfate or a combination thereof.

24. The composition of claim 12, wherein the other excipient(s) comprise one or more agents selected from the group consisting of diluents, disintegrants, wetting agents, anti-adherents, glidants, lubricants, colorants and combinations thereof.

25. The composition of claim 12, wherein the binder is selected from the group consisting of povidone, copovidone, hydroxypropylcellulose, hydroxypropylmethylcellulose, carboxymethylcellulose sodium and combinations thereof.

26. The composition of claim 12, wherein the other excipient(s) comprise one or more agents selected from the group consisting of crospovidone, croscarmellose sodium, sodium starch glycolate, magnesium stearate, stearic acid, sodium lauryl sulfate and combinations thereof.

27. The granulation of claim 1, wherein the granulation has a tapped density (1000 taps) of about 900 mg/cm$^3$.

28. The composition of claim 12, wherein the granulation has a tapped density (1000 taps) of about 900 mg/cm$^3$.

* * * * *